United States Patent [19]

Krüger et al.

[11] Patent Number: 4,699,899

[45] Date of Patent: Oct. 13, 1987

[54] SUBSTITUTED O-SULPHONYL-GLYCOSYLAMIDES, PROCESSES FOR THEIR PREPARATION AND THEIR USE AS MEDICAMENTS

[75] Inventors: Bernd-Wieland Krüger, Wuppertal; Yutaka Hayauchi, Leverkusen; Oswald Lockhoff, Cologne; Peter Stadler, Haan; Karl G. Metzger, Wuppertal; Klaus G. Stünkel, Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 832,482

[22] Filed: Feb. 21, 1986

[30] Foreign Application Priority Data

Mar. 7, 1985 [DE] Fed. Rep. of Germany ....... 3508025

[51] Int. Cl.$^4$ .................... A61K 31/70; C07H 13/00
[52] U.S. Cl. ................................... 514/42; 514/885; 536/18.2; 536/22; 536/53
[58] Field of Search .................... 536/18.2, 53, 22; 514/42, 885

[56] References Cited

U.S. PATENT DOCUMENTS 2,808,404 10/1957 Erickson ........................ 536/22
4,228,274 10/1980 Ponpipom et al. ............... 536/22
4,574,122 3/1986 Kruger et al. .................. 536/53

FOREIGN PATENT DOCUMENTS 0091645 10/1983 European Pat. Off.
0143385 6/1985 European Pat. Off.
0147777 7/1985 European Pat. Off. .......... 514/42
3403495 5/1985 Fed. Rep. of Germany ...... 536/22

OTHER PUBLICATIONS

Carbohydrate Research, vol. 135, No. 2, Jan. 15, 1985, Elsevier Science Publishers B. V., Z. Smiatacz et al.

Primary Examiner—Ronald W. Griffin

Attorney, Agent, or Firm—Sprung Horn Kramer & Woods

[57] ABSTRACT

Novel compounds of the formula

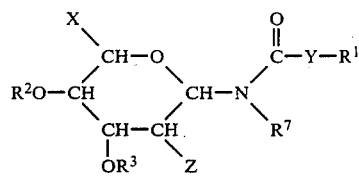

in which
X is hydrogen or —CH$_2$—OR$^5$,
Z represents OR$^4$, NH$_2$ or

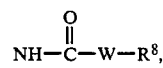

R$^2$, R$^3$, R$^4$ and R$^5$ each independently is hydrogen or

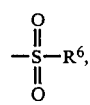

at least one of R$^2$, R$^3$, R$^4$ and R$^5$ being

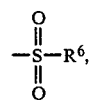

Y and W each independently is oxygen, sulphur, NH or CH$_2$, and
R$^1$, R$^6$, R$^7$ and R$^8$ each independently is an optionally substituted hydrocarbon radical with up to 50 C atoms, stimulate the immune system.

14 Claims, No Drawings

SUBSTITUTED O-SULPHONYL-GLYCOSYLAMIDES, PROCESSES FOR THEIR PREPARATION AND THEIR USE AS MEDICAMENTS

The invention relates to compounds of the general formula I

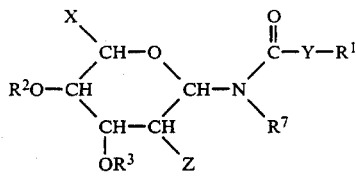

in which
X represents hydrogen or the radical $-CH_2OR^5$,
Z represents $OR^4$ or NHV,
wherein
V denotes hydrogen or

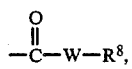

Y and W are identical or different and represent oxygen, sulphur, N—H or $CH_2$,
$R^2$, $R^3$, $R^4$ and $R^5$ are identical or different and represent hydrogen or the radical

with the proviso that at least one of the radicals $R^2$, $R^3$, $R^4$ and $R^5$ denotes

and
$R^1$, $R^6$, $R^7$ and $R^8$ are identical or different and represent an optionally substituted hydrocarbon radical with up to 50 carbon atoms,
processes for their preparation and their use as medicaments.

A carbon radical in the meaning of radicals $R^1$, $R^6$, $R^7$ and $R^8$ is undestood, according to the invention, as meaning a straight-chain or branched alkyl radical, a straight-chain or branched, mono- or polysubstituted unsaturated alkenyl radical, a saturated or unsaturated alicyclic radical or an aromatic radical (aryl). These meanings may also occur together within the same radical $R^1$, $R^6$, $R^7$ and $R^8$, that is to say, for example, as alkylcycloalkyl, arylalkyl, alkylaryl, alkenylcycloalkyl and the like.

In the hydrocarbon radicals $R^1$, $R^6$, $R^7$ and $R^8$, individual, in general up to 5, preferably 1, 2 or 3, methylene or methine groups can also be replaced by O, S and/or N. If the chain is interrupted by N, this nitrogen carries either H or a $C_1$-$C_{20}$—alkyl radical or a —CO—alkyl radical this alkyl group containing 1-20 C atoms.

$R^6$ preferably represents an alkyl radical with 1 to 21 C atoms, preferably with 1-4 C atoms, or represents an optionally substituted aryl radical with up to 21 C atoms, preferably with up to 7 C atoms.

Examples of saturated radicals which may be mentioned here are methyl, ethyl, propyl, i-propyl, butyl and i-butyl. Examples of aryl are halogen-substituted, preferably chlorine- or bromine-substituted, or nitro-, cyano-, amido—$C_1$-$C_4$—alkyl- or $C_1$-$C_4$—alkoxy-substituted phenyl, naphthyl or biphenyl.

Preferably $R^1$, $R^7$ and $R^8$ represent, as desired, alkyl or alkenyl radicals with 1 to 21 carbon atoms, preferably with 9 to 21 C atoms. Examples of saturated radicals which may be mentioned here are methyl, ethyl, propyl, i-propyl, butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, ethylpentyl, methyldecyl, i-propyldecyl, methyltridecyl, eicosyl, tetracosyl, triacontyl, pentahexadecyl, 1-dodecylhexadecyl, 2-dodecylhexadecyl, 3-dodecylhexadecyl, 1-hexadecyloctadecyl, 2-hexadecyloctadecyl, 3-hexadecyloctadecyl, 4-hexadecyloctadecyl, 1-octadecyleicosyl and 2-octadecyleicosyl.

Unsaturated radicals are, for example, vinyl, 1-propenyl, 2-propenyl, i-butenyl, 1-butenyl, 2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-decenyl, 5-decenyl, 9-decenyl, 8-heptadecenyl, 1,3-butadienyl, 1,3-pentadienyl, 1,4-pentadienyl, 2,4-pentadienyl, 8,11-heptadecanedienyl and 8,11,14-heptadecanetrienyl. In general, the longer-chain unsaturated radicals are preferred, especially the mono- or diunsaturated alkenyls with 9-21 C atoms.

The unsaturated hydrocarbon radicals can thereby be present as pure cis- or trans-isomers or as isomer mixtures.

Examples of cycloalkyl which may be mentioned are cyclopentyl, cyclohexyl, decahydronaphthyl and adamantyl.

Examples of alkyl-cycloalkyl and cycloalkyl-alkyl radicals are methylcyclopentyl, ethylcyclopentyl, n-propylcyclopentyl, i-propylcyclopentyl, butylcyclopentyl, octylcyclopentyl, methylcyclohexyl, ethylcyclohexyl, propylcyclohexyl, butylcyclohexyl, hexylcyclohexyl, decylcyclohexyl, cyclopentylmethyl, cyclopentylethyl, cyclopentylpropyl, cyclopentylbutyl, cyclopentylpentyl, cyclopentylhexyl, cyclopentyloctyl, cyclopentyldecyl, cyclohexylmethyl, cyclohexylethyl, cyclohexylpropyl, cyclohexylbutyl, cyclohexylhexyl, cyclohexyldecyl, cyclopentylcyclohexylethyl, cyclohexylcyclopentylethyl and cyclohexylcyclohexylethyl.

Examples of aryl which may be mentioned are phenyl, tosyl, naphthyl and diphenyl.

Examples of aralkyl for $R^1$, $R^7$ and $R^8$ are aryl-lower alkyl, such as benzyl, phenethyl or phenylhexyl.

The radicals $R^1$, $R^6$, $R^7$ and $R^8$ can be substituted, in general 1-5 times, preferably 1-3 times. Preferred possible substituents are the following: halogen, preferably F, Cl or Br, amino, $C_1$-$C_6$—alkylamino, di—$C_1$-$C_6$—alkylamino, oxo, OH, $C_1$-$C_6$—alkoxy, SH, $C_1$-$C_6$—alkylthio, $C_1$-$C_6$—alkyl—COO and $C_1$-$C_6$—alkyl—CO—NH.

Examples of cases in which the hydrocarbon radicals $R^1$, $R^7$ and $R^8$ are interrupted by O, S and N or corresponding atom groupings, or are substituted, for examples, by groups containing these atoms or by halogen atoms, are methoxyethyl, ethoxyethyl, n-propoxyethyl, n-butoxyethyl, i-propoxyethyl, i-butoxyethyl, sec.-butoxyethyl, methoxyethoxyethyl, ethoxyethoxyethyl, propoxyethoxyethyl, i-propoxyethoxyethyl, n-butoxyethoxyethyl, i-butoxyethoxyethyl, sec.-butoxyethoxyethyl, methoxyethoxyethoxyethyl, ethoxyethoxyethoxyethyl, n-propoxyethoxyethoxyethyl, i-propoxyethoxyethoxyethyl, n-butoxyethoxyethoxyethyl, i-butoxyethoxyethoxyethyl and sec.-butoxyethoxyethoxyethyl, if Y and/or Z represent oxygen, sulphur, N-H or $CH_2$; methoxyethoxy, ethoxyethoxy, n-propoxyethoxy, i-propoxyethoxy, n-butoxyethoxy, i-butoxyethoxy, sec.-butoxyethoxy, methoxyethoxyethoxy, ethoxyethoxyethoxy, n-propoxyethoxyethoxy, i-propoxyethoxyethoxy, n-butoxyethoxyethoxy, i-butoxyethoxyethoxy and sec.-butoxyethoxyethoxy, if Y and/or Z represent $CH_2$; and hydroxyheptadecenyl, oxobutyl or the aminodecyl, N-methylaminodecyl, fluoromethyl, β-hydroxytridecyl or mercaptoethyl radical.

The compounds of the formula I contain several chiral C atoms and are present as optical pure diastereomers or as diastereomer mixtures.

The compounds of the formula I according to the invention are thus carboxylic acid amides or N-alkylated or N-aralkylated carboxylic acid amides or carbamic acid, thiocarbamic acid or urea derivatives which additionally carry on the nitrogen atom substituted by the abovementioned radical $R^7$ a single monosaccharide radical which is N-glycosidically bonded, that is to say via the anomeric carbon atom, one or more hydroxyl groups in the saccharide radical being provided with a sulphonyl radical.

Particularly preferred compounds are those in which only one of the radicals $R^2$, $R^3$, $R^4$ or $R^5$ denotes $SO_2$-$R^6$, with the proviso that the other radicals $R^2$, $R^3$, $R^4$ and/or $R^5$ represent hydrogen and $R^6$ and Z have the abovementioned meaning.

Especially preferred compounds are those in which $R^2$, $R^3$ and $R^4$ represent hydrogen and $R^5$ represents the radical $SO_2$—$R^6$, Z and $R^6$ having the abovementioned meaning.

Examples which may be mentioned are:

| Y | Z | $R^1$ | $R^6$ | $R^7$ |
|---|---|---|---|---|
| $CH_2$ | OH | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | " | –⟨⟩–$CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| O | " | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | " | –⟨⟩–$CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| $CH_2$ | " | $(CH_2)_{11}CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | " | –⟨⟩–$CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| O | " | " | $CH_3$ | $(CH_2)_{11}CH_3$ |
| " | " | " | " | $(CH_2)_{13}CH_3$ |
| " | " | " | " | $(CH_2)_{15}CH_3$ |

-continued

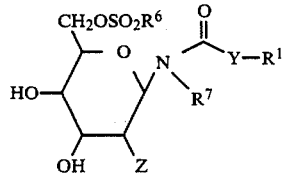

| Y | Z | R¹ | R⁶ | R⁷ |
|---|---|---|---|---|
| " | " | " | " | (CH₂)₁₇CH₃ |
| " | " | " | 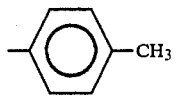 | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | " | (CH₂)₁₃CH₃ | CH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | 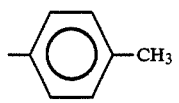 | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| O | " | " | CH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | 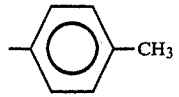 | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | OH | (CH₂)₁₅CH₃ | CH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | 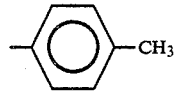 | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| O | " | " | CH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | " | 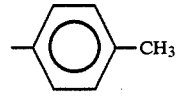 | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| CH₂ | NH₂ | (CH₂)₉CH₃ | CH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |

-continued

[Structure: pyranose ring with CH2OSO2R6 at top, HO, OH, Z substituents, and N(R7)-C(=O)-Y-R1 group]

| Y | Z | R¹ | R⁶ | R⁷ |
|---|---|---|---|---|
| " | " | (CH₂)₁₁CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₃CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₅CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₉CH₃ | —C₆H₄—CH₃ (p-tolyl) | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₁CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₃CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₅CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | NHCOCH₃ | (CH₂)₉CH₃ | CH₃ | (CH₂)₁₁CH₃ |
| " | " | " | " | (CH₂)₁₃CH₃ |
| " | " | " | " | (CH₂)₁₅CH₃ |
| " | " | " | " | (CH₂)₁₅CH₃ |
| " | " | (CH₂)₁₁CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₃CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₅CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₉CH₃ | —C₆H₄—CH₃ (p-tolyl) | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₁CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₃CH₃ | " | (CH₂)₁₁CH₃ |
| " | " | " | " | (CH₂)₁₃CH₃ |
| " | " | " | " | (CH₂)₁₅CH₃ |
| " | " | " | " | (CH₂)₁₇CH₃ |
| " | " | (CH₂)₁₅CH₃ | " | (CH₂)₁₁CH₃ |
| " | " | " | " | (CH₂)₁₃CH₃ |
| " | " | " | " | (CH₂)₁₅CH₃ |

-continued

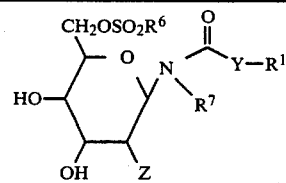

| Y | Z | R¹ | R⁶ | R⁷ |
|---|---|---|---|---|
| " | " | " | " | $(CH_2)_{17}CH_3$ |
| O | " | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_9CH_3$ | ⟨p-tolyl⟩ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | $NH_2$ | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_9CH_3$ | ⟨p-tolyl⟩ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |

-continued

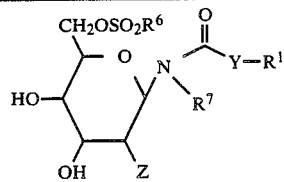

| Y | Z | R¹ | R⁶ | R⁷ |
|---|---|---|---|---|
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| $CH_2$ | $NHCO(CH_2)_{10}CH_3$ | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_9CH_3$ | –C₆H₄–CH₃ (p-tolyl) | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| O | " | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_9CH_3$ | –C₆H₄–CH₃ (p-tolyl) | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |

-continued

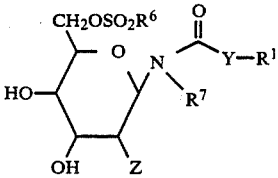

| Y | Z | R¹ | R⁶ | R⁷ |
|---|---|---|---|---|
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| $CH_2$ | $NHCONHCH_3$ | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_9CH_3$ | 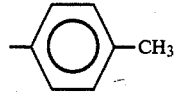 | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| O | " | $(CH_2)_9CH_3$ | $CH_3$ | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |

-continued

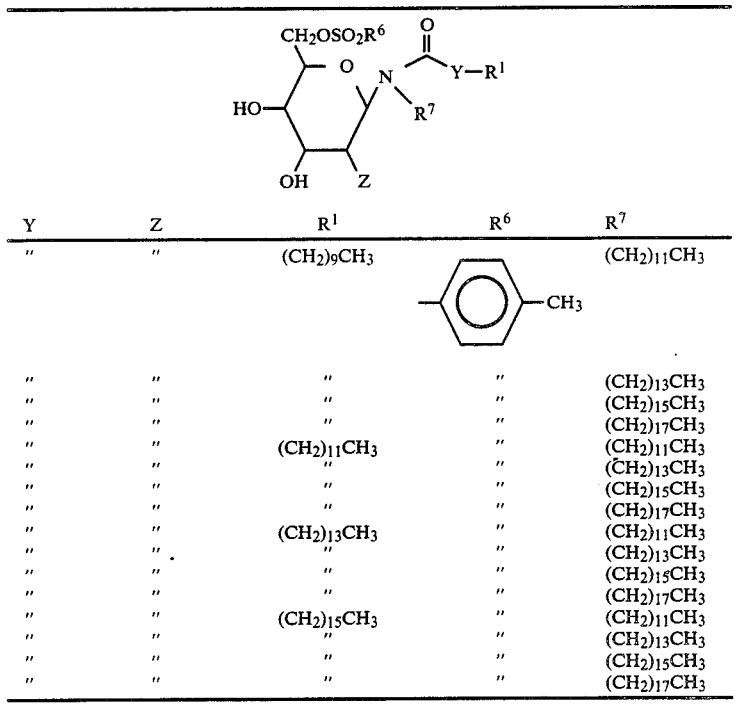

| Y | Z | R¹ | R⁶ | R⁷ |
|---|---|---|---|---|
| " | " | $(CH_2)_9CH_3$ | 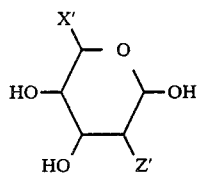 | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{11}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{13}CH_3$ | " | $(CH_2)_{11}CH_3$ |
| " | " . | " | " | $(CH_2)_{13}CH_3$ |
| " | " | " | " | $(CH_2)_{15}CH_3$ |
| " | " | " | " | $(CH_2)_{17}CH_3$ |
| " | " | $(CH_2)_{15}CH_3$ | " | $(CH_2)_{11}CH_3$ |
| " | " | " | " | $(CH_2)_{13}CH_3$ |
| " | " | " | " | $(CH_2)_{15}CH_3$ |
| " | " | " | " | $(CH_2)_{17}CH_3$ |

The invention also relates to processes for the preparation of the compounds of the formula I.

In these, compounds of the formula II $$\text{(II)}$$

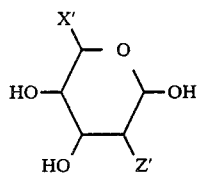

in which

X' represents hydrogen or —CH$_2$OH and
Z' represents OH or NHCO—W—R$^8$, wherein R$^8$ and W have the abovementioned meaning, are first reacted, either in the free, that is to say unprotected, form or in the form of protected, optionally activated derivatives, with an amino compound R$^7$—NH$_2$, either in the free form or in the form of a suitable acid addition salt with the meaning of R$^7$ described above, and the glycosylamine thereby obtained is then acylated with an activated—as is customary in acylation reactions—carboxylic acid, carbonic acid or thiocarbonic acid derivative or isocyanate, protected, if appropriate, on functional groups, any protective groups present in the reaction product thus obtained are split off selectively or completely, and, in a second process step, the intermediate product thus obtained, which is free, that is to say unprotected, on at least one hydroxyl group, is reacted with an activated sulphonic acid derivative which is protected, if appropriate, on functional groups. After any protective groups present have been split off, the compounds of the formula I according to the invention are obtained in this manner and, if necessary, can be purified by chromatography, recrystallisation, extraction or the like.

In a preferred embodiment of the process according to the invention, the unblocked sugar of the formula II is reacted with 1 to 10 equivalents of the amine R$^7$—NH$_2$ in question in a first process step in a manner which is known per se in a suitable solvent or without a solvent, if appropriate in the presence of a catalyst, at temperatures between 0° C. and 80° C. and, after working up, the glycosylamines in question are usually obtained in high yields as amorphous or crystalline solids or as viscous syrups.

In the second process step, the glycosylamine is then reacted with 1 to 10 equivalents of an acyl derivative of the formula R$_1$—Y—CO—X'', in which R$_1$ and Y have the abovementioned meaning and X'' designates halogen or a leaving group which is customary in acylation reactions, preferably an activating ester radical, or a group O—OC—Y—R$_1$, with the above meaning for Y and R$_1$, or 1 to 10 equivalents of an isocyanate of the formula R$^1$—NCO, the reaction being carried out in an organic or aqueous-organic solvent at temperatures between −30° C. and 80° C., if appropriate in the presence of a base, and, when the reaction has ended, the reaction product is worked up in the customary manner.

In a third reaction step, the derivative thus obtained, which has been reacted on the nitrogen, is then reacted, in protected or unprotected form, with 1 to 10 equivalents of a sulphonyl derivative of the formula

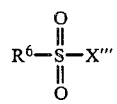

in which

R$^6$ has the abovementioned meaning and
X''' represents halogen, the reaction being carried out in an organic or aqueous-organic solvent at temperatures between −30° C. and 80° C., if appropriate in the presence of a base, and, when the reaction has ended, the reaction product is worked up in the customary manner.

The first process step in the preparation of the compounds of the formula I according to the invention is thus the reaction of a sugar with an amine of the type $R^7$—$NH_2$ on the aromeric carbon atom, water being split off, to give the glycosylamine in question.

Amines $R^7$—$NH_2$ which are liquid at room temperature can be reacted directly with the sugar, that is to say without a solvent. This reaction is carried out at temperatures between 0° C. and 100° C., preferably at 25° C. to 70° C. Suitable catalysts are mineral acids, such as, for example, hydrochloric acid, sulphuric acid or nitric acid, or short-chain carboxylic acids, such as acetic acid or propionic acid, which can be employed in amounts of 0.001 to 0.03 equivalent.

If is in all cases possible, and with amines $R^7$—$NH_2$ which are solid at room temperature also preferable, to carry out the preparation of the glycosylamines in the presence of a solvent. The reaction is then preferably carried out in the presence of a diluent which is inert under the reaction conditions and which is preferably such that at least either the reactants or the reaction products dissolve in it. Possible diluents are alcohols, such as methanol, ethanol, propan-1-ol and propan-2-ol, ethers, such as tetrahydrofuran and dioxane, and also dimethylformamide, the addition of water being preferred-except when alcohols are used. Moreover, in the case of short-chain amines $R^7$—$NH_2$, water by itself is also preferably suitable as the solvent. It may also be advantageous to use the alkanols as a mixture with water.

The reaction temperatures when solvents are used in the preparation of the glycosylamines are between −10° C. and 120° C., preferably between 30° C. and 70° C.

The diluent in question can be added, as desired, before or during the reaction. In the case of long-chain amines $R^7$—$NH_2$, addition before the reaction is preferable.

The glycosylamines prepared as described above crystallize out either directly or after cooling, and can be precipitated or made to crystallize by addition of suitable auxiliary solvents, preferably of low polarity, such as acetone, diethyl ether, cyclohexane, ethyl acetate or petroleum ether, if appropriate with cooling, and any excess amine $R^7$—$NH_2$ present can be removed by washing or recrystallizing the product in a manner which is known per se.

The second process step in the preparation of the compounds of the formula I according to the invention is selective N-acylation of a glycosylamine obtained as described above with an acyl derivative of the formula $R_1$—Y—CO—X″ with the abovementioned meaning of $R_1$, Y and X″, or an isocyanate of the formula $R^1$—NCO.

The third process step in the preparation of the compounds of the formula I according to the invention is selective O-sulphonylation of a protected or unprotected N-acylated aminoglycoside described above with a sulphonyl derivative of the formula

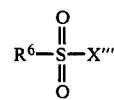

with the abovementioned meaning of $R^6$ and $X'''$.

Preferred carboxyl derivatives $R_1$—Y—CO—X″ which are known per se are anhydrides, activated esters and acid halides, preferably chlorides, and preferred sulphonyl derivatives $R^6$—$SO_2$—$X'''$ which are known per se are acid halides, preferably chlorides.

These compounds are preferably reacted with the glycosyl-amines or -amides in the presence of a diluent in which the reactants are completely or only partly dissolved.

Possible diluents are organic or inorganic solvents, preferably those which as far as possible reduce or prevent side reactions under the reaction conditions. The reaction can be carried out either in organic solvents, such as ethers, for example tetrahydrofuran and dioxane, or alcohols, for example ethanol and propanol, or ketones, for example acetone or methyl ethyl ketone, or in dimethylformamide, ethyl acetate or pyridine, or in mixtures of these solvents with one another and/or with water. The use of anhydrous solvents is generally preferable.

The compounds $R^1$—Y—$COX''$/$R^6$ $SO_2$—$X'''$ or $R^1$—NCO are employed in amounts of 1 to 10 equivalents based on the glycosylamine/glycosylamide.

If acid halides and anhydrides are used, the reactions can preferably be carried out in the presence of basic auxiliaries. All the basic compounds customary in organic synthesis, such as, for example, tertiary aliphatic or aromatic amines or alkali metal and alkaline earth metal hydroxides or carbonates, such as sodium hydroxide solution, sodium carbonate or calcium carbonate, can be used.

The reactions are carried out at temperatures between about −30° C. and +80° C., preferably between −10° C. and +20° C.

In cases where selective reaction of a hydroxyl group cannot be carried out because either a less reactive secondary hydroxyl group of the sugar residue is to be reacted with the radical

with the abovementioned meaning of $R^6$, in the presence of a more reactive primary hydroxyl group, or a secondary hydroxyl group is to be reacted selectively with the radical

in the presence of other secondary hydroxyl groups, or a less reactive hydroxyl group is to be reacted with the radical

with the abovementioned meaning of $R^6$, in the presence of a reactive amino group, the actual sulphonylation reaction is to be preceded by a number of protective group operations in which the hydroxyl group to be reacted with the radical

is selectively present in the free state, that is to say unsubstituted, at the end of the blocking reactions. The hydroxyl groups or amino group which are not to be reacted must thus be blocked before the sulphonylation.

Suitable protective groups for sugar derivatives are described in the relevant literature (for example C. B. Reese, in Protecting Groups in Org. Chem., 1973, pages 95–143; Plenum Press). All the protective groups used in sugar chemistry and combinations thereof can be employed.

Examples of suitable protective groups are esters, such as acetyl, benzoyl, pivaloyl and p-methoxybenzoyl, ethers, such as benzyl, p-methoxybenzyl, allyl and 1-propenyl, alkylidene compounds, such as ethylidene, isopropylidene and benzylidene, ortho-esters, such as 1-methoxy-ethylidene and 1-ethoxy-ethylidene, silyl ethers, such as trimethylsilyl and t-butyldimethylsilyl, and organometallic compounds, such as boric acid esters or tin ethers or tin ketals, such as tributyl-stannyl or dibutyl-stannylidene.

The carbohydrate derivatives blocked by these protective groups are then reacted with the group

on the still free hydroxyl group(s) in a suitable solvent. Suitable solvents and suitable processes for the sulphonylation are those mentioned above.

The O-sulphonylated amides, ureas, carbamates and thiocarbamates obtained in this manner are isolated by processes which are known per se in the form of crystalline or amorphous solids or as viscous syrups and, if necessary, purified by recrystallization, chromatography, extraction and the like.

In the case of compounds with protected hydroxyl or amino groups in the glycosyl part, the protective groups can be split off in a manner which is known per se.

The following equation is intended to illustrate by way of example one of the preferred embodiments of the preparation, according to the invention, of compounds of the formula I:

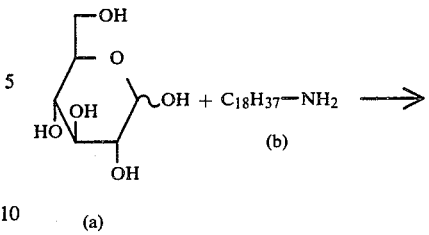

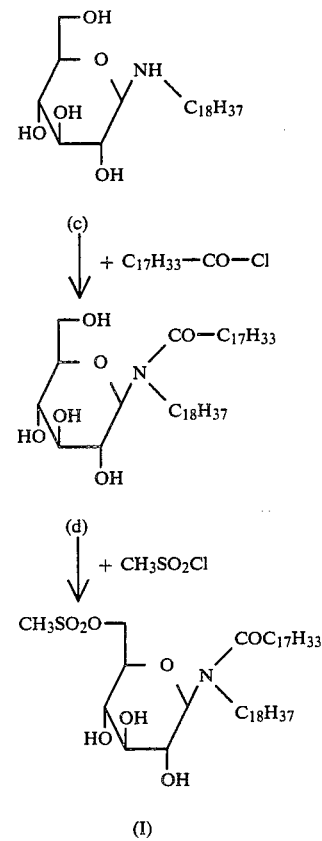

In the first process step, glucose (a) is reacted with octadecylamine (b) to give N-octadecyl-$\beta$-D-glucopyranosylamine (c) which is acylated in the second process step with oleoyl chloride to give N-octadecyl-N-oleoyl $\beta$-D-glycopyranosylamine (d). In the third process step, O-sulphonylation is then carried out in position 6 with methanesulphonyl chloride and N-octadecyl-N-oleoyl-(6-O-methylsulphonyl-$\beta$-D-glycopyranosyl)-amine (I) is obtained.

The invention also relates to salts of the compounds of the formula I. These are, above all, the nontoxic salts which are customarily pharmaceutically usable, for example alkali metal or ammonium salts, or hydrochlorides, hydroacetates or chlorides or acetates.

The compounds of the invention exhibit a pronounced defense-increasing action. It has been found that the class of compound increases antibody synthesis by the immune system in an antigen-specific manner and moreover intensifies the non-specific defense intrinsic to the host. These results have been obtained with the aid of the following experimental design.

Increase in the primary humoral immunity in vitro against sheep erythrocytes (SE).

It is possible experimentally to induce the development of a humoral immune response in heterologous red blood cells by primary immunisation of murine spleen cells in suspension cultures in vitro (R. I. Mishell and R. W. Dutton, J. Exp. Med. 126, 423 (1967)). For this, Balb/c murine spleen cells are cultured for 5 days in the presence of the antigen (SE) and the test substance. The cells are harvested, washed and plated out in semi-solid agar together with the antigen and complement and the agar is incubated for 2 hours at 37° C. (N. K. Jerne, A. A. Nordin and C. Henry, "Cell bound Antibodies", eds. Amos and Koprowski, Wistar Inst. Press, Philadelphia, USA, pages 109 (1963)). Antigen-sensitization of murine lymphocytes in the primary culture results in synthesis and release of antibodies. The specific antibodies discharged bind to the SE-antigen and lyse these cells by the presence of the complement (plaque formation). Substances of the present class of compound are capable of increasing the number of antibody-forming cells dosedependently in the range of 3–100 μg/ml (Table 1).

TABLE 1

Effect of selected O—sulphonyl-glycosylamide analogues of the present classes of compound on antibody synthesis in vitro.

| | Substance Antibody-discharging cells/culture as a function of the dose (μg/ml) | | | | | |
|---|---|---|---|---|---|---|
| Example No. | 0 | 1 | 3 | 10 | 30 | 100 |
| 11 | 1460 | 1840 | 4380 | 4040 | 12,320 | n.p.[1] |
| 8 | 1135 | 3060 | n.p. | 2890 | n.p. | 3240 |
| 10 | 2560 | 2500 | 3020 | 3840 | 6400 | 9560 |
| 14 | 495 | 5380 | 6140 | 11500 | 11520 | 13880 |

[1]not performed

Increase in the primary humoral immunity in vivo against the soluble antigen ovalbumin NMRI mice were immunized subcutaneously (s.c.) with a suboptimum antigen dose (1 μg/animal, day 0). On suboptimum antigen stimulation, only a small number of lymphocytes in the animals were stimulated to antibody synthesis. Additional treatment of the animals with compounds of the examples mentioned from the present invention is capable of significantly increasing the antibody titre in the serum of the animals with a single administration of 10–30 mg/kg subcutaneously. The antibody titre is determined by indirect haemagglutination on day 10. The effect of the treatment is expressed by the geometric mean value of the $\log_2$ titre.

TABLE 2

Adjuvantive effect of selected compound according to the invention in-vivo using the example of the soluble antigen ovalbumin.

| | Dose (mg/kg) | | | |
|---|---|---|---|---|
| Substance Example No. | 0 | 3 | 10 | 30 |
| | Haemagglutination titre (Log2) | | | |
| 7 | 4.0 | 5.4[1] | 5.8 | 6.4 |
| 8 | 4.2 | 5.4 | 5.6 | 6.2 |
| 15 | 4.4 | 5.0[2] | 6.0 | 6.8 |
| 14 | 4.0 | 4.6[2] | 6.2 | 6.6 |

[1]all the values are significantly increased ($p < 0.01$)
[2]not significant

In contrast to other, for example bacterial, immunostimulants, such as LPS from Gram-negative bacteria, the immunostimulating effect of the compounds mentioned is antigen-dependent, that is to say, surprisingly, the substances cause the induction of antibody synthesis only in connection with an antigenic stimulation (in this case SE or ovalbumin). In contrast to the conventional immunostimulants mentioned, they have no mutagenic properties.

Tolerance

Although compounds of the type described already display their potentiating action on mice, for example, after an individual dose of 10 mg/kg intraperitoneally or perorally, no toxic effects are observed even on administration of 100 mg/kg. The substances mentioned therefore have a good tolerance.

The compounds according to the invention have the ability on the one hand to increase the immunogenicity of an antigen when mixed with this antigen, and on the other hand to increase the immunological reactivity of the organism treated on systemic administration. The substances mentioned are thereby capable of activating the lymphocytes responsible for antibody formation.

The new compounds can thus be used as adjuvants, mixed with vaccines, for improving the success of the vaccine and increasing the protection from infection, imparted by immunity, by bacterial, viral or parasitic pathogens.

The compounds described are furthermore suitable, mixed with the most diverse antigens, as adjuvants in the experimental and industrial preparation of antisera for therapy and diagnostics.

The new compounds can moreover also be used without simultaneous supply of antigens to promote defense reactions which already proceed subliminally in humans and animals. The compounds are accordingly particularly suitable for stimulation of the endogenous defense, for example in cases of chronic and acute infection or selective (antigen-specific) immunological defects, and in cases of congenital and also acquired general (that is to say not antigen-specific) immunological defect conditions, such as occur in old age, in the course of severe primary diseases and, above all, after therapy with ionizing radiation or with substances having an immunosuppressant action. The substances mentioned can thus preferably also be administered in combination with anti-infectious antibiotics, chemotherapeutics or other healing methods, in order to counteract immunological damage. Finally, the substances described are also suitable for general prophylaxis of infectious diseases in humans and other animals.

The compounds according to the invention increase the survival rate of acute bacterial infection in animal models.

They can be used by themselves as a prophylactic agent, for combating existing infections or in combination with antibiotic therapy for increasing the therapeutic effect of antibiotics and chemotherapeutics (for example penicillins, cephalosporins, aminoglycosides and the like) on infected humans and animals.

Description of the experiment

It has been found that infections in mice with pathogenic germs which lead to the death of the experimental animals within 24–48 hours can be treated prophylactically—preferably intraperitoneally—with 1–80 mg/kg of the compounds according to the invention. This applies to a large number of Gram-positive (for example Staphylococci) and Gram-negative (for example E. coli, Klebsiella, Proteus and Pseudomonas) pathogens.

This list is by way of example and is in no way to be interpreted as limitative. Thus, for example, 40 to 100% of mice which have been infected with the pathogenic strain Klebsiella 63 survived this infection after treatment (for example 18 hours before infection) with 10–40 mg/kg of the compound according to the invention in Example 7, 8 and 11, while only 0 to 30% of the untreated control animals survived.

In another experimental model, it has been possible to show that the therapeutic efficacy of antibiotics can be increased by the compounds according to the invention. Thus, mice were infected with the strain Pseudomonas W. This infection leads to death within 24 hours in most control animals. Another group was treated with 4 mg/kg of sisomycin 30 hours after infection. It was possible to show that it was possible decisively to improve the therapeutic efficacy of the sisomycin in the experimental group which had been treated with the compounds according to the invention (for the examples, see above) 18 hours before infection.

The pharmaceutical products of the present invention are preferably tablets or gelatin capsules, which contain the active compounds together with diluents, for example lactose, dextrose, sucrose, mannitol, sorbitol and cellulose, and/or lubricants, for example silica, talc, stearic acid or salts thereof, such as magnesium stearate or calcium stearate, and/or polyethylene glycol. Tablets also contain binders, for example magnesium aluminum silicate, starches, such as corn starch, wheat starch, rice starch or arrowroot starch, gelatin, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescent mixtures, or adsorbents, colorants, flavor substances and sweeteners. Injectable products are preferably isotonic aqueous solutions or suspensions. Suppositories, ointments or creams are above all fat emulsions or suspensions. The pharmaceutical products can be sterilised and/or can contain auxiliaries, for example preservatives, stabilizers, wetting agents and/or emulsifying agents, solubilizing agents, salts for regulating the osmotic pressure and/or buffers. The present pharmaceutical products, which, if desired, can contain other pharmacologically useful substances, are prepared in a manner which is known per se, for example by means of conventional mixing, granulating or coating processes, and contain from about 0.1% to about 75%, in particular from about 1% to 50%, of the active substances mentioned.

The orally administered products of the present invention can also be provided with a coating which is resistant towards gastric juice.

The compounds according to the invention can be used as defence-increasing and immunopotentiating agents for the treatment of chronic and acute infections (for example bacterial, viral and parasitic) and malignant tumours. They can also be used as adjuvants in vaccination, in stimulation of phagocytosis and in dysregulation of the defence and immune system.

EXAMPLES

EXAMPLE 1

N-Octadecyl-D-glucopyranosylamine 20 g of octadecylamine are dissolved in 120 ml of ethanol and the solution is warmed to 70°. 11 g of anhydrous D-glucose are added. After a clear solution has formed, stirring is continued at 70° for a further 15 minutes. The mixture is cooled to 10° and left to stand for 15 minutes. The crystal sludge formed is filtered off with suction, washed twice with ethanol and dried in vacuo.

Elemental analysis: calculated: C 66.8% H 11.4% N 3.2%: found: C 67.4% H 11.8% N 3.7%.

EXAMPLE 2

N-Glucopyranosyl-N-octadecyl-dodecanoic acid amide 10 g of the compound from Example 1 are suspended in 20 ml of tetrahydrofuran and, after addition of 10 g of sodium carbonate, 10 g of dodecanoyl chloride in 10 ml of tetrahydrofuran are added dropwise. When the reaction has ended (control by thin layer chromatography on silica gel 60 in toluene/isopropanol 6:1), the solid is filtered off, the filtrate is evaporated to a syrup in vacuo and the crude product is purified by column chromatography on silica gel 60 with the eluting agent toluene/isopropanol 10:1.

$\alpha_D = 8°$ (c = 1.0 in dioxane)

EXAMPLE 3

N-Dodecyl-D-galactopyranosylamine

Preparation from D-galactose and dodecylamine according to Example 1.

Elemental analysis calculated: C 62.2% H 10.7% N 4.0%: found: C 62.5% H 10.2% N 4.4%.

EXAMPLE 4

N-Galactopyranosyl-N-dodecyl-octadecanoic acid amide

Preparation according to Example 2 from 10 g of the compound according to Example 3 and 16 g of stearoyl chloride.

$\alpha_D = 4.4°$ (c = 1.0 in methylene chloride)
Rf value = 0.23 in toluene/n-propanol 4:1

EXAMPLE 5

N-Octadecyl-N-(D-glucopyranosyl)-decylurethane 9 g of the compound from Example 1 were suspended in 160 ml of tetrahydrofuran and 40 ml of ethanol, and 9 g of sodium carbonate were added. 5 g of decyl chloroformate, dissolved in 40 ml of tetrahydrofuran, are added dropwise to this suspension in the course of 20 minutes. When the reaction has ended, the batch is filtered and the residue on the filter is rinsed with tetrahydrofuran. The filtrate is combined with the wash solutions and evaporated in vacuo. The resulting syrup is purified by chromatography (mobile phase methylene chloride/methanol, 20:1)

Rf value: 0.37 in $CH_2Cl_2/CH_3OH$ 10:1 Elemental analysis: calculated: C 68.3% H 11.3% N 2.3%: found: C 68.4% H 11.6% N 2.4%.

EXAMPLE 6

N-Octadecyl-N-(D-glucopyranosyl)-N'-dodecylurea 9 g of the compound from Example 1 are suspended in 160 ml of tetrahydrofuran and 40 ml of ethanol. 4.3 g of dodecyl isocyanate, dissolved in 20 ml of tetrahydrofuran, are added dropwise to this suspension in the course of 20 minutes. When the reaction has ended, the mixture is evaporated in vacuo and the resulting syrup is purified by column chromatography (mobile phase methylene chloride/methanol, 15:1)

Rf value: 0.33 in $CH_2Cl_2/CH_3OH$ 10:1
$\alpha_D = 7.4°$ (c = 1.04 in dioxane)

Example 7

N-Octadecyl-N-dodecanoyl-(6-O-methylsulphonyl-β-D-glucopyranosyl)-amine

9.2 g (0.015 mol) of N-glucopyranosyl-N-octadecyl-dodecanoic acid amide are dissolved with 7 g (0.064 mol) of triethylamine in 100 ml of tetrahydrofuran, and 3.4 g (0.03 mol) of methanesulfonyl chloride, dissolved in 10 ml of tetrahydrofuran, are added dropwise at an internal temperature of −20° C. The mixture is then stirred at 20° C. for 2 days, the solid is filtered off and the filtrate is concentrated to a syrup in vacuo. This crude product is then purified by column chromatography on silica gel 60 with the eluting agent toluene/isopropanol 10:1.

Yield: 4.5 g (43% of theory).

Rf value=0.345 (toluene: isopropyl alcohol=6:1)

The following compounds can be prepared analogously:

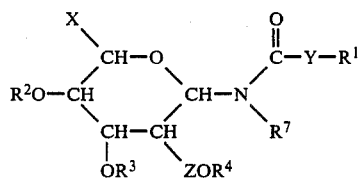

in which

X is hydrogen or —$CH_2OR^5$,

Z represents $OR^4$, $NH_2$ or

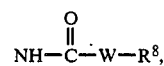

$R^2$, $R^3$, $R^4$ and $R^5$ each independently is hydrogen or

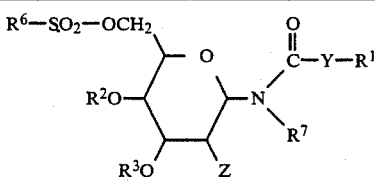

$R^2, R^3 = H$

| Example | Sugar | $R^1$ | Y | Z | $R^7$ | $R^6$ | Rf value (toluene: isopropyl alcohol = 6:1)* |
|---------|-------|-------|---|---|-------|-------|----------------------------------------------|
| (8) | Glucose | $(CH_2)_{13}CH_3$ | O | OH | $(CH_2)_{11}CH_3$ | $CH_3$ | 0.310 |
| (9) | Mannose | $(CH_2)_{15}CH_3$ | $CH_2$ | " | $(CH_2)_{13}CH_3$ | $CH_3$ | 0.402 |
| (10) | Glucose | $(CH_2)_9CH_3$ | $CH_2$ | " | $(CH_2)_{17}CH_3$ | —C$_6$H$_4$—CH$_3$ | 0.491 |
| (11) | Galactose | $(CH_2)_{15}CH_3$ | $CH_2$ | " | $(CH_2)_{11}CH_3$ | —C$_6$H$_4$—CH$_3$ | 0.455 |
| (12) | Glucose | $(CH_2)_{15}CH_3$ | $CH_2$ | $NHCOCH_3$ | $(CH_2)_{11}CH_3$ | $CH_3$ | 0.200 |
| (13) | Glucose | $(CH_2)_9CH_3$ | $CH_2$ | " | $(CH_2)_{11}CH_3$ | $CH_3$ | 0.173 |
| (14) | Galactose | $(CH_2)_{15}CH_3$ | $CH_2$ | OH | $(CH_2)_{11}CH_3$ | $CH_3$ | 0.345 |
| (15) | Mannose | $(CH_2)_9CH_3$ | $CH_2$ | OH | $(CH_2)_{17}CH_3$ | $CH_3$ | 0.257 |
| (16) | Mannose | $(CH_2)_9CH_3$ | $CH_2$ | OH | $(CH_2)_{13}CH_3$ | —C$_6$H$_4$—CH$_3$ | |
| (17) | Glucose | $(CH_2)_{15}CH_3$ | $CH_2$ | OH | $(CH_2)_{13}CH_3$ | —C$_6$H$_4$—CH$_3$ | |

*Thin layer chromatography aluminum foils, Merck, silica gel 60 F 254, 0.2 mm

It will be understood that the specification and examples are illustrative but not limitative of the present invention and that other embodiments within the spirit and scope of the invention will suggest themselves to those skilled in the art.

What is claimed:

1. A compound of the formula

at least one of $R^2$, $R^3$, $R^4$ and $R^5$ being

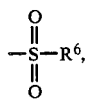

Y and W each independently is oxygen, sulphur, NH or CH₂, and

R¹, R⁶, R⁷ and R⁸ each independently is an unsubstituted or substituted hydrocarbon radical with up to 50 carbon atoms, said substituted hydrocarbon radical containing a substituent selected from the group consisting of F, Cl, Br, amino, C₁–C₆-alkylamino, di—C₁–C₆—alkylamino oxo, OH, C₁–C₆—alkoxy, SH, C₁–C₆—alkyl—thio, C₁–C₆—alkyl—COO and C₁–C₆—alkyl—CO—NH.

2. A compound according to claim 1, in which the hydrocarbon radicals R¹, R⁶, R⁷ and R⁸ have up to 21 carbon atoms.

3. A compound according to claim 1, in which the hydrocarbon radicals R¹ and R⁷ have 9–21 carbon atoms, R⁶ has up to 7 carbon atoms and R⁸ has up to 21 carbon atoms.

4. A compound according to claim 1, in which
R², R³ and R⁴ each is hydrogen,
X is CH₂OR⁵ or CH₂OSO₂R⁶,
Z is OR⁴ and
R⁵, R⁶ and W are as defined as in claim 1.

5. A compound according to claim 1, in which
R² and R³ each is hydrogen
X is CH₂OSO₂R⁶,

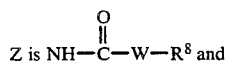

R⁶, R⁸ and W are as defined as in claim 1.

6. A compound according to claim 1, wherein the compound is N-octadecyl-N-dodecanoyl-(6-0-methylsulphonyl-β-D-glucopyranosyl)-amine of the formula

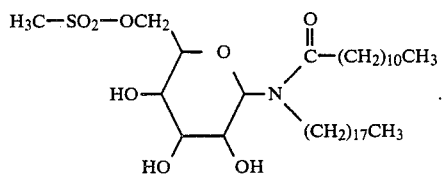

7. A compound according to claim 1, wherein the compound is N-dodecyl-N-(6-0-methylsulphonyl-β-D-gluco-pyranosyl)-tetradecylurethane of the formula

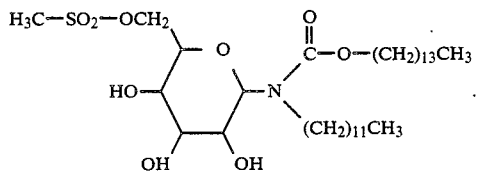

8. A compound according to claim 1, wherein the compound is N-octadecyl-N-dodecanoyl-(6-0-p-tolylsulphonyl-β-D-glucopyranosyl)-amine of the formula

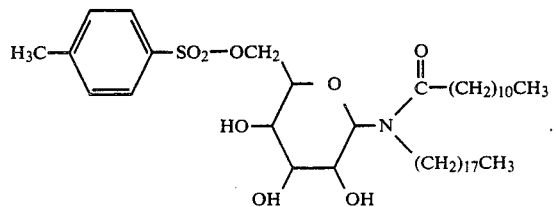

9. A compound according to claim 1, wherein the compound is N-dodecyl-N-octadecanoyl-(6-0-p-tolylsulphonyl-β-D-galactopyranosyl)-amine of the formula

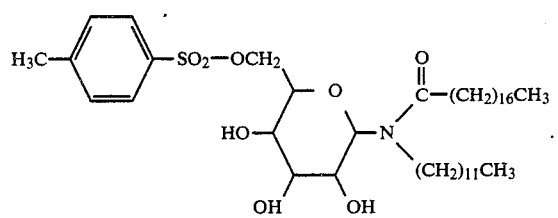

10. A compound according to claim 1, wherein the compound is N-dodecyl-N-octadecanoyl-(2-acetylamino-2-deoxy-6-0-methylsulphonyl-β-D-glucopyranosyl)-amine of the formula

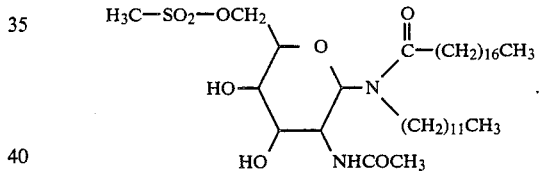

11. An immunostimulating composition comprising an immunostimulating effective amount of a compound according to claim 1 in admixture with a pharmaceutically acceptable carrier.

12. A unit dose of a composition according to claim 11 in the form of a tablet, capsule or ampule.

13. A method of stimulating the immune system of an animal which comprises administering thereto an immunostimulating effective amount of a compound according to claim 1.

14. The method according to claim 13, wherein such compound is
N-octadecyl-N-dodecanoyl-(6-0-methylsulphonyl-β-D-glucopyranosyl)-amine,
N-dodecyl-N-(6-0-methylsulphonyl-β-D-glucopyranosyl)-tetradecylurethane,
N-octadecyl-N-dodecanoyl-(6-0-p-tolylsulphonyl-β-D-glucopyranosyl)-amine,
N-dodecyl-N-octadecanoyl-(6-0-p-tolylsulphonyl-β-D-galactopyranosyl)-amine or
N-dodecyl-N-octadecanoyl-(2-acetylamino-2-deoxy-6-0-methylsulphonyl-β-D-glucopyranosyl)-amine.

* * * * *

UNITED STATES PATENT AND TRADEMARK OFFICE
CERTIFICATE OF CORRECTION

PATENT NO. : 4,699,899
DATED : October 13, 1987
INVENTOR(S) : Bernd-Wieland Krüger, et al.

It is certified that error appears in the above-identified patent and that said Letters Patent is hereby corrected as shown below:

| | |
|---|---|
| Col. 1, line 52 | Correct spelling of --understood-- |
| Col. 17, line 20 | Delete "0.03" and substitute --0.05-- |
| Col. 17, line 21 | Delete "If" and substitute --It-- |
| Col. 20, lines 49,53 | Correct --glucopyranosylamine-- |
| Col. 21, line 20 | Delete "dosedependently" and substitute --dose-dependently-- |
| Col. 21, line 51 | Delete "compound" and substitute --compounds-- |
| Col. 26, line 8 | Bottom of formula delete "ZOR$^4$" and substitute --Z-- |
| Col. 27, line 55 | Delete "gluco-pyransoyl" and substitute --glucopyranosyl-- |

Signed and Sealed this

Thirty-first Day of May, 1988

Attest:

Attesting Officer

DONALD J. QUIGG

Commissioner of Patents and Trademarks